United States Patent [19]
Ruhrmann

[11] Patent Number: 4,936,681
[45] Date of Patent: Jun. 26, 1990

[54] OPTICAL SENSOR

[76] Inventor: Wolfgang Ruhrmann, Herrenberger Straße, Stuttgart 80, Fed. Rep. of Germany, 24 D-7000

[21] Appl. No.: 214,733
[22] PCT Filed: Aug. 28, 1987
[86] PCT No.: PCT/DE87/00383
§ 371 Date: May 3, 1988
§ 102(e) Date: May 3, 1988
[87] PCT Pub. No.: WO88/01738
PCT Pub. Date: Mar. 10, 1988

[30] Foreign Application Priority Data
Sep. 3, 1986 [DE] Fed. Rep. of Germany ....... 3629966

[51] Int. Cl.$^5$ .............................................. G01N 21/41
[52] U.S. Cl. ................................ 356/133; 250/227.25; 250/227.31; 250/577; 250/905; 356/375; 73/293
[58] Field of Search ........................ 356/128, 133, 375; 250/227, 577; 73/293; 340/619

[56] References Cited
U.S. PATENT DOCUMENTS
4,544,840 10/1985 Keller .................................... 356/133

FOREIGN PATENT DOCUMENTS
| 0006317 | 5/1979 | European Pat. Off. . |
| 0115025 | 12/1983 | European Pat. Off. . |
| 2034344 | 7/1970 | Fed. Rep. of Germany . |
| 2155049 | 11/1971 | Fed. Rep. of Germany . |
| 3243839 | 11/1982 | Fed. Rep. of Germany . |
| 3321217 | 6/1983 | Fed. Rep. of Germany . |
| 3403887 | 2/1984 | Fed. Rep. of Germany . |
| 3428453 | 8/1984 | Fed. Rep. of Germany . |
| 3433343 | 9/1984 | Fed. Rep. of Germany . |
| 3527082 | 7/1985 | Fed. Rep. of Germany . |
| 2085831 | 4/1971 | France . |
| 5553878 | 10/1978 | Japan . |
| 0202330 | 10/1985 | Japan .................................. 356/133 |

Primary Examiner—F. L. Evans
Attorney, Agent, or Firm—Pretty, Schroeder, Brueggemann & Clark

[57] ABSTRACT

An optical sensor for converting a physical value into an electric output signal comprises a light source from which a beam of light rays is coupled into a first surface of a photoconductive body. The light rays are totally reflected by one boundary surface of, or coupled out from said body in response to a given physical value. The totally reflected light rays impinge upon a second face. A plurality of light-sensitive elements is provided for detecting the angular range $\beta$ covered by the beam after it has been totally reflected or coupled out, respectively. In order to enable the sensor to be adapted to a plurality of applications and in order to obtain reproducible, digitized output values, independently of any local disturbing factors or long-term phenomena, the body is designed as an elongated waveguide in which light rays are subjected to multiple total reflection. The light-sensitive elements are arranged at an axial distance h from a waveguide face. They form a surface of impingement for the beam of light rays emanating from the face. The elements are connected to an evaluation circuit comprising a counter which emits a digital output signal representative of the number of elements illuminated by the beam.

27 Claims, 4 Drawing Sheets

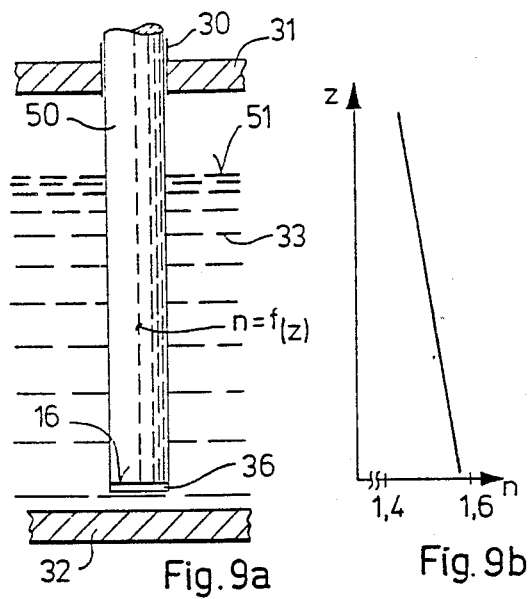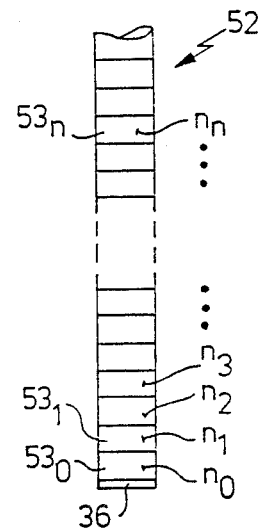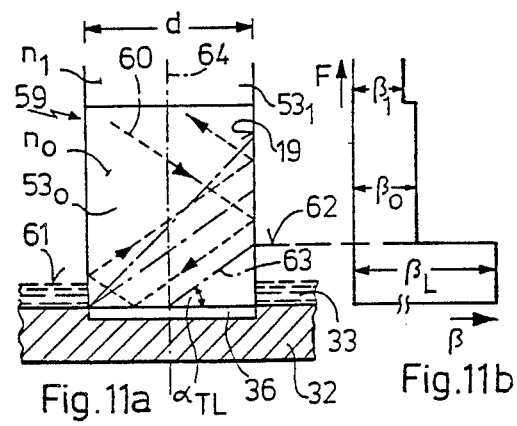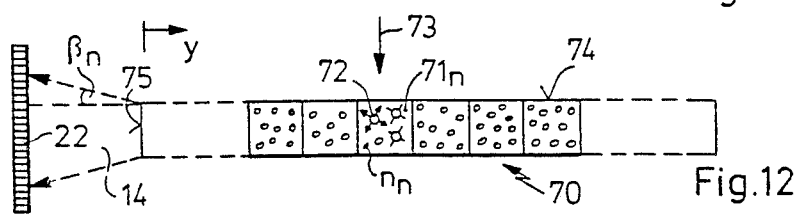

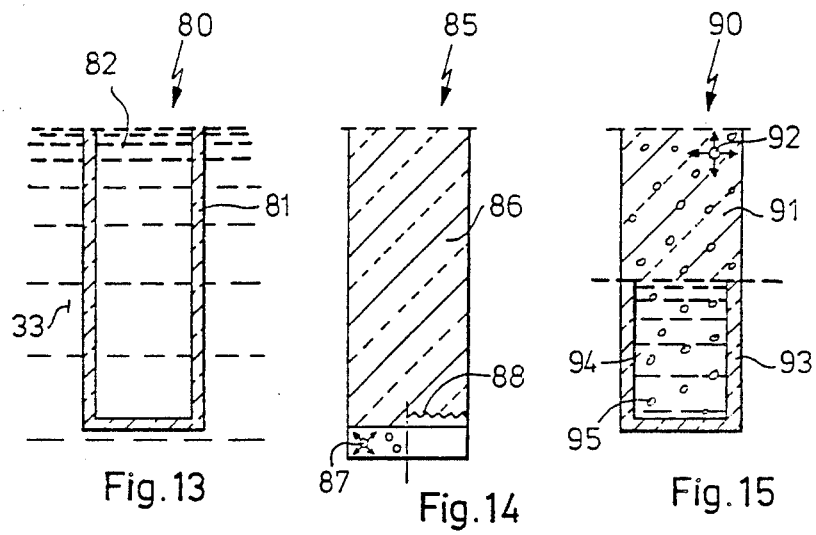
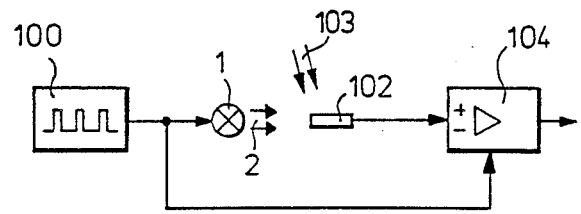
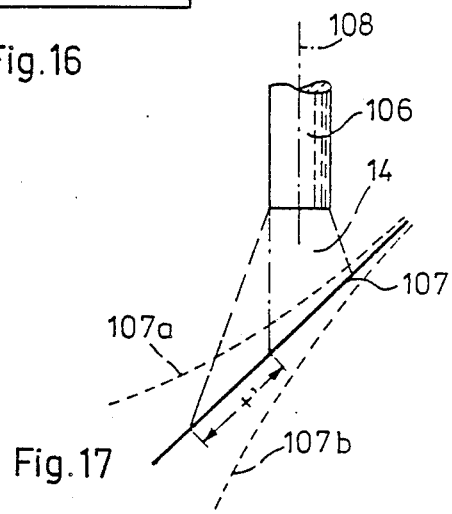

OPTICAL SENSOR

The present invention relates to an optical sensor for converting a physical value into an electric output signal, comprising a light source from which a beam of light rays is coupled into a first surface, preferably a first front face of a photoconductive body, the light rays being totally reflected by one boundary surface of, or coupled out from the said body in response to a given physical value and the totally reflected light rays being directed to a second rear face provided preferably opposite the said first face, and comprising further a plurality of light-sensitive elements for detecting the angular range covered by the beam after it has been totally reflected or coupled out as described.

A sensor of this type has been known from "Patents abstracts of Japan", June 21, 1980, Vol. 4/87.

The known sensor serves for measuring the concentration of the electrolyte of a lead storage battery. It comprises a light source emitting a diverging beam of rays which passes a diaphragm and impinges upon an inclined lateral surface of a prismatic photoconductive body. A lower, elongated boundary surface of the body is provided adjacent the electrolyte to be measured. The light rays of the diverging beam of rays impinging upon the lower boundary surface are either totally reflected by the latter or coupled out from the body into the electrolyte, depending on their angle of impingement and the density of the electrolyte. The totally reflected light rays impinge upon another, likewise inclined boundary surface of the prismatic body carrying a gate consisting of light-sensitive elements. Depending on the density of the electrolyte to be measured, the boundary between the light rays of the beam which are still totally reflected or, on the other hand, coupled out varies at the lower interface between the prismatic body and the electrolyte with the effect that the corresponding boundary line of the totally reflected light rays impinging upon the gate of light-sensitive elements changes, too. Given the fact that a partial beam is always reflected by the lower boundary surface, even if a certain amount of light rays is coupled out, one obtains an intensity curve rising abruptly from a relatively low signal level to a relatively high signal level, viewed over the length of the gate of light-sensitive elements. The known sensor now picks up the amplitude of the light rays impinging upon the different elements of the gate and uses the respective position on the gate of the abrupt rise of the signal level as a measure indicative of the density of the electrolyte.

However, it is a drawback of this known sensor that it must be adjusted very precisely because due to the single total reflection of the light rays by the prismatic body even very slight maladjustments of the impinging beam of light rays may already seriously invalidate the measuring results. In addition, the known sensor is connected with the disadvantage that in practice the density of the electrolyte is measured only in a point-like area, namely in a very small portion of the length of the boundary surface where the transition between total reflection and coupling out varies so that the measuring results are characteristic of the condition of the whole electrolyte contained in a vessel, for example in a storage battery, if the electrolyte contained in the battery actually exhibits uniform density. However, this is not always the case in practice because on the one hand lighter, for example warmer portions of the electrolyte tend to collect in the upper portion of the storage battery, while heavier portions will settle at the bottom, and in addition considerable variations in density over the volume of the battery may result from movements of the type occurring, for example, in motor vehicles. The known sensor is not capable of measuring the acid density between the plates of an accumulator, and its installation in pipes is difficult, too. Another disadvantage of the known sensor lies in the fact that it is always suited for a single measuring task only, namely for measuring the density of the fluid adjoining the prismatic body. Finally, it is another drawback of the known sensor that the measuring results are obtained in analog form because the system measures the signal intensity at the individual elements of the gate. This provides the risk of the measuring result being invalidated by drift effects of all kinds, for example by aging phenomena encountered in the optical elements involved.

There have further been known numerous other sensors which transform physical values into electric output signals by optoelectronic means utilizing the refraction characteristics of a waveguide. However, it is a general feature of all these sensors that they also provide analog measured values; only in connection with sensors used for fluid level detection has it been known to indicate the fact that a threshold value has been exceeded in the form of a digital Yes/No signal; but continuous digital liquid level indication is also not possible with these sensors.

Now, it is the object of the present invention to improve a sensor of the type described above so as to render it suited for a plurality of measuring tasks, and insensitive to maladjustments, and to ensure that any local disturbing factors encountered in the environment of the sensor remain without effect and, finally, to enable the respective output signals to be indicated continuously in digital form.

This object is achieved according to the invention by an arrangement which is characterized in that the body takes the form of an elongated waveguide in which light rays are subjected to multiple total reflection, that the light-sensitive elements are arranged at an axial spacing from one end face and form a surface of impingement for a beam of light rays emanating from the said end face, and that the elements are connected to an evaluation circuit comprising a counter emitting a digital output signal representative of the number of elements illuminated, or not illuminated by the light beam. Hereafter, only the method of counting the illuminated elements will be described in detail. If the number of elements which are not illuminated is to be counted and evaluated, then the total number of all elements must be known.

This solves the object underlying the present invention fully and perfectly. The use of an elongated waveguide providing multiple total reflection avoids, on the one hand, any adjustment problems because one anyway obtains uniform light ray conditions over the length of the waveguide, while on the other hand any discontinuities that may occur in the environment of the waveguide are also averaged out. The fact that the rays are guided in the waveguide makes the system suited for performing numerous different measuring tasks. For example, it is rendered possible in this way, as in the case of the known sensor described above, to measure the index of refraction and, thus, also the density of a fluid surrounding the waveguide, independently of its state of aggregation, or to carry out continuous level measurements. In addition, it is also possible to measure geometrical values, in particular lengths, in this way. It is, however, understood that this list of possible applications is by no means intended to restrict the application range of the invention.

Another considerable advantage of the invention is seen in the fact that the angle range of the beam emerging from the waveguide or, to say it in other words, the so-called "acceptance cone" is measured in digital form by counting and indicating the number of elements illuminated at the given magnitude of the physical value. Consequently, the measuring results are not affected by aging phenomena or other drift phenomena because the evaluation circuit for each light-sensitive element has to decide only between Yes and No so that the intensity of the impinging light ray and/or the manner in which the conversion factor between the impinging light ray and the voltage supplied has changed in the element itself due to aging phenomena is without any importance for the element, provided the triggering threshold has been suitably adjusted.

Altogether, the invention therefore provides a universally useful, sturdy, reliable sensor which is insensitive to aging phenomena.

According to a preferred embodiment of the invention, the light-sensitive elements are arranged at an axial spacing from the second face.

This feature leads to a particularly simple structure of the waveguide because in the case of a cylindrical waveguide, for example, the beam of light rays is coupled into the one radial end face and the acceptance cone of the light beam emerging from the opposite radial face is measured.

According to another embodiment of the invention, the second face is designed as a reflector and the light-sensitive elements are provided at an axial distance from the first face.

This feature provides the advantage that although a somewhat more complex structure has to be accepted the sensor must be accessible only from one side, i.e. the side on which the light is initially coupled into the sensor and then coupled out again for measuring the acceptance cone. A sensor designed in this way is, therefore, particularly well suited for performing measuring tasks at points which are not easily accessible, for example for measuring the density or the liquid level in a fully contained vessel.

According to a variant of this embodiment of the invention, the waveguide is subdivided into two axially spaced sections, and the beam is coupled into the first face of the first axial portion, while the light-sensitive elements are provided at an axial distance from the first face of the second section.

Another variant serving similar purposes provides that the first face comprises two axially spaced steps and that the beam is coupled into the forward step, while the light-sensitive elements are arranged at an axial distance from the rear step.

These two variants provide the common advantage that the light source emitting the beam of light rays can be physically separated from the light-sensitive elements for measuring the acceptance cone because the two processes occur at axially spaced points of the waveguide.

According to another embodiment of the invention, the surface of impingement is inclined relative to the axis of the waveguide.

This feature provides the advantage that by varying the acceptance cone as a result of the inclination of the surface of impingement, one obtains an increase of the range within which the edge of the acceptance cone varies.

According to a preferred further development of this variant, the surface of impingement may also have a predetermined curved shape for compensating in this manner any existing non-linearities of the sensor.

According to a first example of an application of the invention, the physical value to be measured is the density of a fluid surrounding the waveguide and the waveguide is optically coupled to the fluid only by its second face.

According to one variant of this example, the waveguide may be optically coupled to the fluid only by its cylindrical surface.

These features provide the advantage that the structure of the sensor can be adapted optimally to the space available at the measuring point.

The waveguide may be optically coupled to the fluid by both its second face and its cylindrical surface, whereby the sensitivity of the system can be increased still further.

According to the invention, the medium may be a fluid of variable density, although it is also possible to measure gases with variable pressure because the density of the gas varies as a function of the pressure.

In a different field of application of the sensor according to the invention, the physical value to be measured is the level of a liquid. In this case, the waveguide is submerged in the liquid over part of its axial length, and the optical index of refraction of the waveguide decreases from its lower end towards its top. To express this in more general terms, the physical value to be measured is the position of an interface between two media, for example between two liquids, having different indices of refraction.

This feature provides the advantage that continuous level measurements, including the generation of digital indications, are rendered possible because the generating angle of the acceptance cone is determined at any time by the lowest index of refraction which in the case of the described gradient of the index of refraction over the axial length of the waveguide is exactly the one encountered on the surface of the surrounding liquid. To say it in other words: the generating angle of the acceptance cone decreases continuously from a maximum value obtained at minimum filling level to a minimum value obtained at maximum filling level, this variation of the acceptance cone being transformed into a digital value in the manner described before.

According to a further development of this variant, the waveguide according to the invention exhibits axially adjacent sections having different optical indices of refraction.

This feature provides the advantage that the waveguide is easier to produce because existing materials can be used for the different sections.

According to one further variant of this embodiment of the invention, the waveguide is sized in such a manner that the product of half its thickness and the tangent of the total-reflection interfacial angle of the waveguide material situated outside the measuring fluid, relative to the surrounding fluid, is considerably smaller than, preferably ⅓ to 1/40 of, the length of the waveguide.

This feature provides the advantage that in the case of extremely low liquid levels a big signal step is obtained at the moment when the liquid level rises above or drops below a level corresponding to the product of half the thickness of the waveguide and the tangent of the before-mentioned interfacial angle. Before this level is reached, the acceptance cone exhibits a very big generating angle which corresponds to the interfacial angle between the waveguide and the surrounding medium outside the fluid (generally air), while at the moment when this level is passed, the generating angle drops suddenly to a very much lower value corresponding to the interfacial angle between the waveguide and the liquid. This signal step is considerably larger in the case of the waveguide materials under discussion than the steps obtained in the case of waveguides with stepped index of refraction, as discussed in the preceding paragraph. Accordingly, the very important signal step can be utilized with advantage as "reserve indication" to warn the user of the sensor that the liquid has dropped to a very extreme lower threshold value.

In certain embodiments of the invention, the waveguide consists of glass or a plastic material, for example polymethylacrylate (PMMA).

This feature provides the advantage that known materials of likewise known and reproducible properties can be used.

In the case of other variants of the invention, the waveguide comprises a transparent tube filled with a reference medium whose chemical composition corresponds, at a predetermined magnitude of the physical value, to that of the medium to be measured which surrounds the tube.

This feature which has been known as such from DE-PS No. 34 02 374, provides the advantage that the characteristics of the reference medium and the surrounding medium to be measured vary uniformly with any variation of the surrounding conditions so that here again any drift phenomena are excluded.

According to another variant of the present invention, the waveguide comprises light-emitting elements which emit secondary light after having been irradiated with primary light.

This feature provides the advantage that instead of irradiating diffuse light into the waveguide, the use of a parallel beam of light is also possible, in which case the diffuse rays required for the purposes of the invention are then represented by the secondary light. This can be achieved, for example, by causing the light to impinge upon impurity spots (color centers) in the waveguide, providing diffusely reflecting interfaces upon which the primary light impinges, or by providing the waveguide with luminescent centers generating themselves secondary light.

This embodiment of the invention is particularly well suited for a third field of application of the invention where the physical value is a length. It is provided in this case that the optical index of refraction of the waveguide increases in the axial direction, starting from the face of the waveguide, that the beam of light rays impinges laterally upon the waveguide at a radial distance from the face equal to the length, and that the light-sensitive elements are arranged at an axial spacing from the face.

This embodiment of the invention, which therefore also makes use of the central idea of the invention, namely to provide a digital indication of the variation of the acceptance cone, therefore provides the advantage to permit contactless length measurements because—depending on the index of refraction of the luminescent waveguide section upon which radial measuring ray impinges—the end face of the waveguide is left by a beam whose acceptance cone is a function of the index of refraction of the before-mentioned waveguide area.

In the case of this embodiment of the invention, it is also possible, as described before in connection with the application for liquid level measurements, to use either a waveguide with continuously varying index of refraction or a stepped waveguide with sections of different indices of refraction.

Finally, another embodiment of the invention is preferred where the light source is connected to a pulse generator and the evaluating circuit comprises a subtractor circuit whose inputs can be supplied with the measured values obtained with the light source switched on and switched off.

This feature provides the advantage that extraneous light influences can be measured and, thus, compensated by measurements taken during the pulse intervals.

Other advantages of the invention will be apparent from the following description and the attached drawing.

It is understood that the features that have been described above will be explained hereafter, can be used in any embodiment of the invention not only in the described combinations, but also in any other combination or individually, without leaving the scope of the present invention.

Certain embodiments of the invention will now be described in greater detail with reference to the drawing in which:

FIGS. 9a and 9b show one embodiment of a sensor according to the invention, for measuring a fluid level, and the related characteristic of the index of refraction, over the length of the waveguide used;

FIG. 10 shows a variant of the embodiment of FIG. 9a, using a stepped waveguide;

FIGS. 11a to 11c show details of the sensor according to FIG. 9a or FIG. 10, illustrating a reserve indication arrangement rendered possible by the invention;

FIG. 12 shows one embodiment of the sensor according to the invention, for measuring a length;

FIG. 13 shows a first variant of a configuration of a waveguide according to the invention, for use in connection with any of the sensors of FIGS. 5 to 11;

FIG. 14 shows a second variant thereof;

FIG. 15 shows a third variant thereof, but for use in connection with any of the sensors of FIGS. 5 to 12;

FIG. 16 shows a largely schematized circuit diagram, illustrating the circuit arrangement of a sensor according to the invention; and FIG. 17 shows another variant, similar to that of FIG. 1, for improving the measuring sensitivity of a sensor according to the invention.

Figure 1:
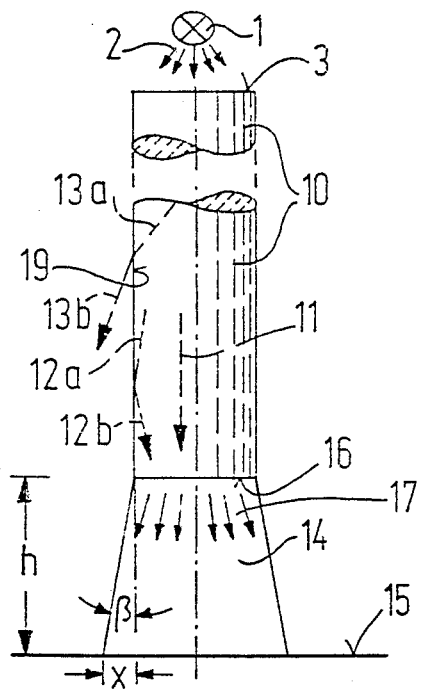
FIG. 1 shows a diagrammatic representation of a waveguide illustrating the present invention.

In FIG. 1, reference numeral 1 designates a light source emitting a diverging beam of rays 2 which enters a neighboring upper face 3 of a cylindrical optical waveguide 10. The point-shaped light source 1 with the diverging beam of rays 12 is to be understood as an example only; as will be explained further below it is also possible to use parallel beams of rays from which diverging secondary light is then derived inside the waveguide.

In FIG. 1, one can see a first axially directed ray 11 passing through the waveguide 10 without being deflected or obstructed in any way. Reference numerals 12a, 12b designate a second light ray which impinges upon a cylindrical surface 19 of the waveguide 10 at such a flat angle that it is totally reflected. The light ray 12a, 12b, therefore, also continues its way through the waveguide 10 in the axial direction. In contrast, reference numerals 13a, 13b designate a third light ray which impinges upon the cylindrical surface 19 at such a great angle that it is coupled out from the waveguide 10.

All this leads to the condition that following several reflection processes in the waveguide 10, the only light rays 11 or 12a, 12b left are those which are directed in an absolutely axial direction or at an angle flat enough to ensure their total reflection by the cylindrical surface 19. One thereby obtains a so-called "acceptance cone" 14, which term describes the shape of a diverging beam 17 of light rays emerging from a lower face 16 of the waveguide 10.

A surface of impingement 15 is defined at an axial distance h from the lower end face 16. If the generating angle of the acceptance cone 14 is designated by $\beta$ and if the lower face 16 exhibits a circular shape, one obtains at the surface of impingement 15 a circular illuminated surface and a surrounding annular area of a radial width x which is a function of the angle $\beta$ and the axial distance h.

Now, when the total-reflection interfacial angle changes due to variations in the refraction conditions in the waveguide 10 or in the surrounding medium, the angle $\beta$ and, consequently, the dimension x will change, too.

Figure 2:
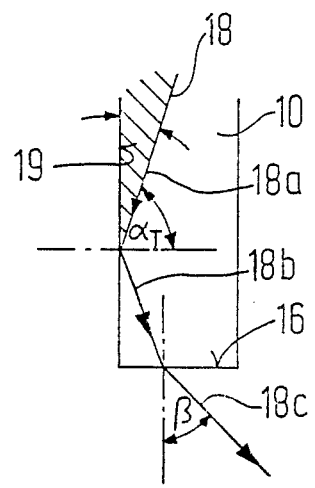
FIG. 2 shows a representation of a path of rays as encountered in the waveguide according to FIG. 1.

FIG. 2 illustrates once more the conditions represented in FIG. 1, for quantifying the effects obtained. It be assumed for the present purpose that a fourth light ray 18 is guided in the waveguide 10, and that its section 18a impinges upon the cylindrical surface 19 exactly at the total-reflection interfacial angle $\alpha_T$. Concretely, this means that all light rays impinging within the shaded area of FIG. 2 are totally reflected, while all rays impinging at a greater angle than the light ray 18 are coupled out from the waveguide 10. The section 18a of the ray 18 is (still) totally reflected, and a reflected section 18a impinges upon the lower face 16. Assuming that the ray section 18b impinges upon the lower face 16 at a point outside of the total-reflection area defined by the particular refraction conditions prevailing at the lower face 16, a section 18c of the ray 18 is coupled out from the lower face 16 at an angle $\beta$ corresponding exactly to the generating angle $\beta$ of the acceptance cone 14 in FIG. 1.

If the index of refraction of the waveguide 10 is designated by $n_i$, the index of refraction of the medium surrounding the waveguide 10 in the area of its cylindrical surface 16 by $n_a$, and the index of refraction of the medium surrounding the waveguide 10 at the lower face 16 by $n_{st}$, it can be shown that the generating angle $\beta$ of the acceptance cone 14 is determined by the following relationship:

$$\sin\beta = \sqrt{n_i^2 - n_a^2}\,/n_{st}$$

it being understood that $n_i$ is greater than $n_a$ and $n_{st}$. If the refraction conditions existing at the cylindrical surface 19 and at the end face 16 are equal, i.e. if $n_a = n_{st}$, this will simplify the above formula accordingly.

It is, therefore, apparent that the width x in FIG. 1, related to the generating angle $\beta$ and the distance h, provides a direct measure of the refraction conditions of the waveguide 10, relative to the surrounding medium.

Now, it is provided according to the invention that the width x is output as measured value, in digitized form.

Figure 3:
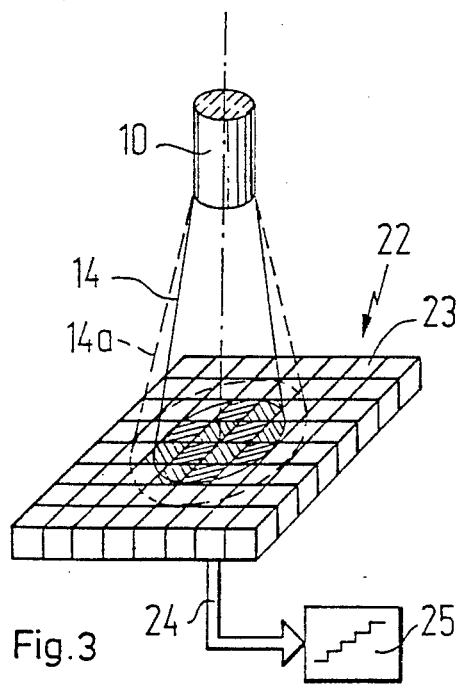
FIG. 3 shows a first embodiment of a flat light-measuring arrangement, for use in connection with the sensor according to the invention.

FIG. 3 shows one corresponding embodiment of the invention, where again the waveguide 10 can be seen from which a beam of rays emerges in the form of the acceptance cone 14. An additional acceptance cone 14a shown in broken lines symbolizes a second measured value.

Below the waveguide 10, one can see, at a certain axial distance from the imaginary surface of impingement, a flat detector array 22 designed, for example, as a charge-coupled device (CCD). The detector array 22 comprises a plurality of detector elements 23 which are distributed over a surface and which can be controlled and read out individually. A data line indicated at 24 leads to an evaluation circuit 25 comprising essentially a digital counter.

In the example illustrated by the acceptance cone 14 drawn in full lines, the 8 detector elements—shaded in FIG. 3—are illuminated so that when these elements have been counted via the data line 24 a digital value "8" is outputted by the evaluation circuit 25. By selecting a corresponding number of detector elements 23, it is possible to obtain almost any desired resolution of the measuring result and by setting a triggering threshold for partially illuminated detector elements 23 one can further preset a threshold value for recognizing a detector element 23 as illuminated or not illuminated, provided this should be desirable for practical purposes. It is even possible in this manner to define precisely any gray transitions that may be encountered in the marginal area of the acceptance cone.

It is easily seen in FIG. 3 that when the acceptance cone 14 is enlarged to a cone 14a (shown in broken lines), a correspondingly greater number of detector elements 23 is illuminated so that a correspondingly higher digital value is supplied at the output of the evaluation circuit 25.

Figure 4:
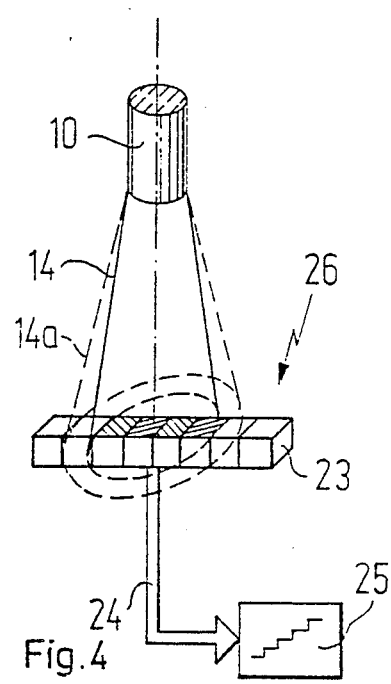
FIG. 4 shows a variant of the embodiment of FIG. 3, with a linear light-measuring arrangement.

FIG. 4 shows a variant where the distance x according to FIG. 1 is determined by measurement along a straight line, instead of the surface measurement according to FIG. 3. This is achieved by a linear detector array 26, for example a linear diode gate or the like. One can see in FIG. 4 that in the case of the acceptance cone 14 shown in full lines, four detector elements 23—which are again shaded in FIG. 4—are illuminated while six detector elements are illuminated in the case of the enlarged acceptance cone 14a. The number of illuminated detector elements is again counted and outputted by the evaluation circuit 25 in the form of a digital value.

FIGS. 5 to 8 illustrate four embodiments where the sensor according to the invention is used for measuring the density of a surrounding medium, in particular a fluid.

Figure 5:
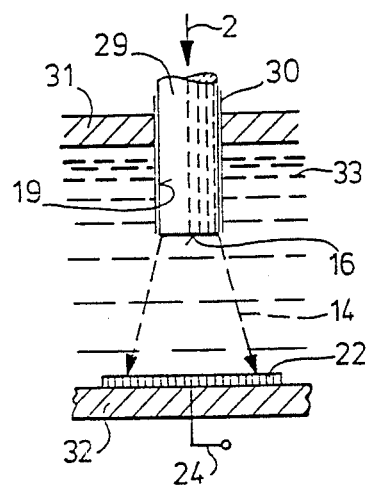
FIG. 5 shows a first variant of this sensor, for measuring the density of a medium.

In the embodiment shown in FIG. 5, an optical waveguide 29 is surrounded in the area of its cylindrical surface 19 by a mirror coating 30 so that light is permitted to emerge only from the lower end face 16. The waveguide 29 is passed through a bore in a wall 31 of a fluid vessel. The detector array 22 is arranged on an opposite wall 32, and its, data line 24 is passed to the outside through the wall 32 spaced from the lower face 16. A waveguide 29 is surrounded by a fluid 33 whose density is to be measured. The mirror coating 30 may consist of a metal or a transparent cladding having a lower index of refraction than the waveguide 29 itself.

The beam of rays 2 entering the upper end—not shown in the drawing—of the waveguide 29 passes the waveguide 29 in the axial direction. As no rays can penetrate through the cylindrical surface 19, due to the mirror coating 30, they emerge from the lower face 16 of the waveguide 29 and this, due to the optical mechanism described before, only within the acceptance cone 14 which is then measured in the described manner by means of the detector array 22.

Given the fact that the refraction conditions existing at the lower face 16 vary in response to the density of the fluid 33 to be measured, the generating angle of the acceptance cone 14 provides a direct measure, in the arrangement shown in FIG. 5, for the density of the fluid 33.

It is understood that instead of including a fluid 33, the walls 31, 32 may also include between them a gas whose density varies in response to the gas pressure, in which case it is possible to measure the gas pressure.

FIG. 5 may be modified by substituting a light source for the elements 22 and arranging the elements 22 at an axial distance above the upper face—not shown in the drawing—of the waveguide 29.

Figure 6:
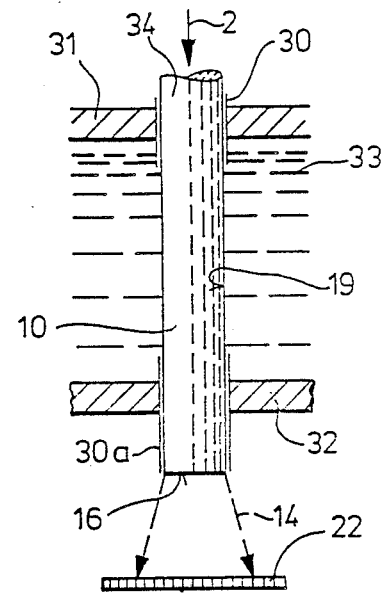
FIG. 6 shows a second variant thereof.

FIG. 6 shows another embodiment of the invention used for density measurements, where a waveguide 34 is passed through aligned openings in the walls 31, 32 of the vessel containing the fluid 33 to be measured. The cylindrical surface 19 is provided with mirror coatings 30, 30a only in the areas of these passages, while the rest of the cylindrical surface 19 is surrounded directly by the fluid 33.

In this case, the beam of rays in the form of the acceptance cone 14 emerges from the waveguide 34 outside of the vessel, and impinges upon the axially spaced detector array 22 for being processed in the described manner.

While in the case of the embodiment illustrated in FIG. 6 the measurement is determined by the refraction conditions prevailing in the area of the cylindrical surface 19 of the waveguide 34, the results of the measurement are identical to those obtained by the arrangement of FIG. 5.

Figure 7:
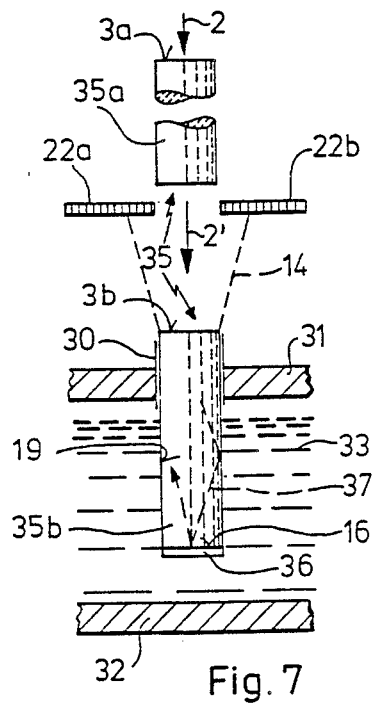
FIG. 7 shows a third variant thereof.

FIG. 7 shows another variant of this arrangement where a waveguide 35 is subdivided into two axially offset sections 35a, 35b. The upper section 35a is provided with an upper face 3a for coupling in the beam 2. Below the lower face of the upper section 35a, there is provided either a flat detector array comprising an opening which is aligned with the waveguide 35, or two lateral, separate detector arrays 22a, 22b, as shown in FIG. 7, leaving between them a corresponding space as passage for the beam 2' emerging from the bottom face of the upper section 35a.

The lower section 35b passes through a bore in the wall 31 of the vessel for the fluid 33. Except for a mirror coating 30 provided in the area of the passage through the wall 31, the lower section 35b exhibits no mirror coating on its cylindrical surface 19 and is directly surrounded by the fluid 33. In contrast, the lower face 16 is provided with a mirror 36 or another suitable reflector. This means that when a light beam 37 guided through the lower section 35b impinges upon the mirror 36 it is reflected upwardly so that a beam of rays in the form of the acceptance cone 14 emerges from an upper face 3b of the lower section 35b. The generating angle of the acceptance cone 14 is then measured by the detector array 22a, 22b in the described manner.

Figure 8:
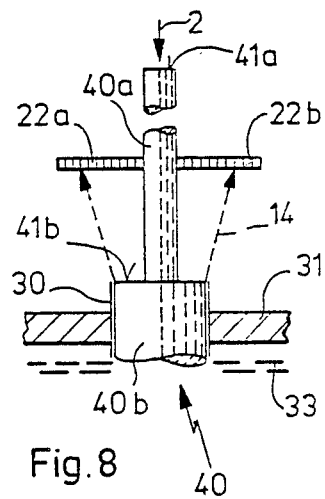
FIG. 8 shows a fourth variant thereof.

According to FIG. 8, a waveguide 40 which passes again through the upper wall 31 of the vessel containing the fluid 33 comprises a lower section of larger diameter in the area of this passage which is followed on top by a section 40a of smaller diameter. The lower section 40b, therefore, exhibits an annular end face 41b, while the upper section 40a exhibits a circular end face 41a. Entering through this face 41a, the beam of rays 2 passes to the lower section 40b, the lower portion of the sensor according to FIG. 8 being designed in the same manner as that of the sensor according to FIG. 7. The light reflected by the mirror—not shown in FIG. 8—at the lower end of the waveguide 40 then leaves the waveguide through the circular end face 41b of the lower section 40b and impinges upon the detector array 22a, 22b, which is again designed in the same way as that of FIG. 7.

Another group of embodiments of the invention, as shown in FIGS. 9 to 11, enables the level of a fluid to be measured by means of a sensor according to the invention.

FIG. 9a shows for this purpose an elongated waveguide 50 which is submerged over part of its axial length in the fluid 33 to be measured which is in turn contained in the vessel provided with the walls 31, 32. The lower end face 16 of the waveguide 50 is again provided with a mirror 36 so that the measuring arrangement is generally identical to that illustrated in connection with the formula given in connection with FIGS. 7 or 8 for the case of density measurements.

However, it is an additional particularity of the arrangement shown in FIG. 9a that the index of refraction n of the waveguide 50 varies over its axial length z. The development of the index of refraction n over the axial length z is illustrated in FIG. 9b, and it is clearly seen that the index of refraction n reaches its maximum of approx. 1.6 at the lower end and its minimum of approx. 1.4 at the upper end.

As has been stated already at the outset, in connection with the general explanations relating to the function and operation of the sensors according to the invention, with reference to FIGS. 1 and 2, the generating angle $\beta$ of the acceptance cone 14 is the smaller the greater the index of refraction of the waveguide material is. Concretely, this means that when the waveguide material exhibits a low index of refraction, more and more rays are coupled out from the waveguide until only those rays are guided in the waveguide which extend at a very flat angle, i.e. almost in parallel to the waveguide axis. If the index of refraction varies over the length of the waveguide, this means that the acceptance cone is delimited and, accordingly, defined by that area of the waveguide which exhibits the lowest index of refraction.

In the case of the embodiment illustrated in FIGS. 9a and 9b this is—related to the fluid 33—always that area of the waveguide 50 which is located adjacent the surface of the fluid 33, i.e. which defines the fluid level 51.

Accordingly, when the fluid level 51 as shown in FIG. 9a drops from an upper maximum value to a lower minimum value, this means that the acceptance cone emerging from the upper end—not shown in the drawing—of the waveguide 50 will increase its generating angle $\beta$ as the fluid level 51 decreases, whereby digital level measurements are rendered possible in the manner described with reference to FIGS. 3 and 4.

In the case of the waveguide 50, exhibiting the refraction index gradient represented in FIG. 9b, this characteristic can be obtained, for example in the case of a waveguide consisting of a plastic material, by adjusting the degree of polymerization over the length of the waveguide. It is, however, also imaginable to change the index of refraction by subjecting the waveguide selectively to pressure, radiation or the like.

Instead of using a waveguide 50 exhibiting a continuously varying index of refraction n, as shown in FIG. 10, one may also use a waveguide 52 which is subdivided into a plurality of axially adjacent sections 53. The sections $53_0$, $53_1$.... $53_n$ are designed in such a manner that their indices of refraction $n_0$, $n_1$, $n_2$... $n_n$ decrease from the bottom to the top. Accordingly, the characteristic shown in FIG. 9b for the waveguide 50 of FIG. 9a would be generally similar, although slightly stepped, in this case.

Each of the sections 53 may in addition exhibit a continuously varying index of refraction n so that the stepped sections 53 would provide a coarse measurement, while the axially varying index of refraction n would permit an additional precise measurement within the respective section 53.

FIGS. 11a to 11c illustrate an additional phenomenon which is obtained in waveguides 50 according to FIGS. 9a, 9b or 52 according to FIG. 10 and which is of particular advantage if small residual quantities of fluid 33 are to be indicated. Such an indication may be of particular advantage, for example, for fuel tanks in motor vehicles when a "reserve fuel indication" is to be supplied in a particularly clear manner in order to warn the driver that the fuel supply has dropped below a pre-determined minimum quantity.

For the purpose of explaining this phenomenon illustrated in FIGS. 11a to 11c, we initially refer to FIG. 11c where a waveguide 59 of the width d and a longitudinal axis 64 is shown. In the lower portion of the waveguide 59, the two total-reflection interfacial angles $\alpha_{TL}$ relating to the waveguide 59 in surrounding air, and $\alpha_{TF}$ relating to the waveguide 59 in surrounding fluid 33, can be seen.

In FIG. 11a, a ray 60 entering the waveguide from above is inclined exactly at the interfacial angle $\alpha_{TL}$ for surrounding air, which means that it is totally reflected by the cylindrical surface 19 of the waveguide 59 which is surrounded by air. In the case of the very low level 51 illustrated in FIG. 11a, this means that—although a very small lower portion of the waveguide 59 is still surrounded by fluid 33—this ray 60 is reflected by the mirror 36 and the cylindrical surface 19 to the upper end of the waveguide 59 where it defines an acceptance cone whose generating angle is defined by the interfacial angle $\alpha_{TL}$ for surrounding air and is, therefore, very large.

This reflection of rays 60 which are inclined at angles up to the interfacial angle $\alpha_{TL}$ for surrounding air, is possible until the fluid 61 in the vessel reaches the level 62 shown in FIG. 11a. The level 62 is defined by the line of intersection of a cone 63 drawn about the axis 64 of the waveguide 59, the exterior angle of the cone 63 being exactly equal to the interfacial angle $\alpha_{TL}$ for surrounding air. Once the fluid level exceeds the level 62, the rays 60 can no longer be reflected towards the upper end of the waveguide 59. Rather, the system assumes the condition illustrated in FIG. 11c which means that in the presence of a higher filling level 65 the ray 60 is coupled into the fluid 33 because now the refraction conditions of the cylindrical surface 19 of the waveguide 59 are defined by the larger interfacial angle $\alpha_{TF}$ for surrounding fluid.

Regarding now the characteristic of the generating angle $\alpha$ of the acceptance cone, as a function of the filling level F, as shown in FIG. 11b, it can be seen that up to the level 62 the generating angle $\beta$ assumes the value $\alpha_L$ which—as has been explained before—is defined by the interfacial angle $\alpha_{TL}$ for surrounding air. Once the filling level exceeds the level 62, the value of the generating angle $\beta$ drops abruptly to the value $\beta_0$ which is defined by the interfacial angle $\alpha_{TF}$ for surrounding fluid.

If the waveguide is stepped along its axial length, as shown at 52 in FIG. 10, additional steps $\beta_1$ etc., may follow, as shown in the upper portion of FIG. 11b, but these steps are then considerably smaller than the lowest step from $\beta_L$ to because the limit values $\alpha_T$ will never jump again by such a big step.

The very important signal step from $\beta_L$ to $\beta_0$ can, therefore, be utilized for activating a reserve fuel indication. As is easily apparent from FIG. 11a, the activation point of this reserve fuel indication may be determined easily by appropriate selection of the thickness d of the waveguide 59, in relation to the interfacial angle $\alpha_{TL}$ for surrounding air.

The sensors according to the invention find a third field of application in the measurement of geometrical values, in particular of the length y, as illustrated by way of example in FIG. 12.

A waveguide 70 is subdivided in the axial direction into sections 71. In FIG. 12, one of these sections is designated by reference numeral $71_n$. The sections 71 consist of a luminescent material, and one of the luminescent elements contained in the sections $71_n$ is designated by reference numeral 72. The sections 71 exhibit again different indices of refraction, the index of refraction of section $71_n$ being designated by $n_n$. The values of the indices of refraction decrease from one section to the next—in FIG. 12 from the right to the left.

A narrow beam of rays or a ray 73 directed radially to the waveguide 70 impinges upon a lateral surface 74 of the waveguide 70, thereby exciting luminescence in one of the sections 71. The secondary light emitted by the respective luminescence element 72 as a result thereof propagates in the axial direction of the waveguide 70. At the end of the waveguide 70, the secondary light directed towards the left in FIG. 12 impinges upon a radial end face 75 and emerges therefrom in the form of an acceptance cone 14 so that the generating angle $\beta_n$ of the acceptance cone 14 can be measured by means of the detector array 22 in the manner described before.

Given the fact that the index of refraction n of the sections 71 increases towards the end face 75, the generating angle of the acceptance cone 14 is determined in each case by that section 71 upon which the ray 73 originally impinges, because each of the sections located closer to the end face 75, in the direction of radiation, permits a larger acceptance cone 14 although this latter is not utilized for lack of suitably "steep" rays.

It is therefore possible to determine the section 71, upon which the ray 73 originally impinged, by measuring the generating angle $\beta_n$. To say it in other words, the generating angle $\beta_n$ provides a measure for the length y if y is defined as the distance between the ray 73 and the forward end face 75.

It is of course also possible in this manner, by a corresponding extension of the arrangement in the plane, to provide sensors suited for measuring the location of an impinging point of light in the plane.

FIGS. 13 to 15 show some variants of waveguides which are each suited for some of the embodiments illustrated in FIGS. 1 to 12.

FIG. 13 shows initially a variant where a waveguide 80 is formed substantially by a transparent tube 81, for example a glass tube, filled with a reference medium 82. The reference medium 82 is either of the same chemical kind as the surrounding medium, for example the fluid 33, or differs from the latter in a defined manner so that disturbance variables can be eliminated.

If, for example, the waveguide 80 is used for measuring the density of an acid, the same acid may be used as the reference medium 82 in which case its density corresponds to a specific reference value of the acid serving as fluid 33 to be measured. Under these circumstances, any external influences affecting both the fluid to be measured and the reference medium will remain without effect on the measuring results.

FIG. 14 shows another variant where the waveguide 85 consists substantially of a transparent body 86 made of glass, a plastic material or the like. However, as can be seen in the left half of FIG. 14, a luminescent body 87 is arranged at the lower end of the waveguide 85, although it is also possible to provide a diffuse reflector 88, as shown in the right half of FIG. 14.

It is therefore possible with the aid of the waveguide 85 to apply to the sensor a parallel beam of rays ending at its lower end in a diffuse, secondary or reflected beam of rays emitting rays in upward direction, at different inclinations. Such an arrangement may be used with advantage, for example, in the embodiments illustrated in FIGS. 7 and 8.

FIG. 15 shows a variant where a waveguide 90 consists again of a transparent body 91 comprising an array either of luminescent elements 92 or of diffusion elements, for example color centers, or the like.

As can be seen in the lower half of FIG. 15, the same effect can be achieved also with fluids, as in the case of the embodiments according to FIG. 13, by providing a glass tube 93 filled with a reference fluid 94 of a predetermined chemical composition with suspended particles 95 contained therein.

It is possible in this manner, too, to use secondary light in different manners as reflected light or light generated by secondary emission for being reflected by the boundary surfaces of the waveguide in a diffuse manner, or for being coupled out.

FIG. 16 shows a largely schematized circuit diagram of a circuit arrangement for operating a sensor according to the invention.

A pulse generator 100 operates the light source 1 which, consequently, supplies a pulsating beam of light 2 to a waveguide 102. The latter is additionally exposed to extraneous light 103. The waveguide 102 is connected to an amplifier 104 by suitable detector and evaluation means of the type explained with reference to FIGS. 3 and 4, and the amplifier 104 is further connected to the output of the pulse generator 100.

The circuit arrangement according to FIG. 16 serves the purpose to eliminate the influence of the extraneous light 103. To this end, the signal originating exclusively from the extraneous light 103 and received by the waveguide 102 is determined and stored in the amplifier 104 during the pulse intervals of the pulse generator 100. During each pulse of the pulse generator 100, an actual value is formed from the effects resulting in the waveguide 102 from the beam of light 2 emanating from the light source 1 and the influence of the extraneous light 103, and the actual value of the extraneous light 103 which has been determined before is subtracted from this actual value. Given the fact that as a rule the extraneous light 103 is an invariable disturbance factor, it is possible in this manner to compensate the influence of the extraneous light 13.

FIG. 17 finally shows another possibility of increasing the width x in FIG. 1, for the purpose of improving the measuring accuracy by improved resolution.

A waveguide 106 similar to that shown in FIG. 1 has its lower end arranged at an axial distance from an impingement surface 107 which is, however, inclined relative to a longitudinal axis 108 of the waveguide 107. One obtains in this manner an increased width x' when the beam of light rays impinges on the impingement surface 107 in the form of the acceptance cone 14.

In FIG. 17 it is further shown at 107a, 107b that the impingement surface 107 can be given a curved shape, either in addition to or instead of the inclination relative to the axis 108, in order to compensate or to generate certain characteristics, depending on what is desirable in the particular case.

I claim:

1. An optical sensor for converting a physical value into an electric output signal, comprising a light source from which a beam of light rays is coupled into a first surface of a photoconductive body, said light rays being totally reflected by one boundary surface of, or coupled out from said body in response to a given physical value and said totally reflected light rays being directed to a second face provided opposite said first face, and comprising further a plurality of light-sensitive elements for detecting an angular range $\beta$ covered by said beam after it has been fully reflected or coupled out, respectively, wherein said body takes the form of an elongated optical waveguide in which said light rays are subjected to multiple total reflection, said light-sensitive elements being arranged at an axial spacing h from an end face and forming a surface of impingement for a beam of light rays emanating from said end face, said elements being connected to an evaluation circuit comprising a counter emitting a digital output signal representative of the number of elements illuminated, or not illuminated by said light beam.

2. The sensor of claim 1, wherein said first surface is a first front face and said second face is a rear face of said waveguide.

3. The sensor of claim 1, wherein said light-sensitive elements are arranged at an axial spacing h from said second face.

4. The sensor of claim 1, wherein said second face is designed as a reflector and said light-sensitive elements are arranged at an axial spacing h from said first face.

5. The sensor of claim 4, wherein said waveguide is subdivided into two axially spaced sections, said beam being coupled into a first face of a first of said axial sections, while said light-sensitive elements are provided at an axial distance from a first face of a second of said axial sections.

6. The sensor of claim 4, wherein said first face comprises a forward step and a rearward step, axially spaced with respect to each other, said beam being coupled to said forward step, while said light-sensitive elements are arranged at an axial distance from said rear step.

7. The sensor of claim 1, wherein said surface of impingement is inclined relative to a longitudinal axis of said waveguide.

8. The sensor of claim 1, wherein said surface of impingement has a predetermined curved shape.

9. The sensor of claim 1, wherein said physical value is an index of refraction and, accordingly, corresponds to a density of a medium surrounding said waveguide, said waveguide being optically coupled to said medium only by said second face.

10. The sensor of claim 1, wherein said physical value is a density of a medium surrounding said waveguide, said waveguide being optically coupled to said medium only by a cylindrical waveguide surface.

11. The sensor of claim 9, wherein said medium is a fluid or variable density.

12. The sensor of claim 10, wherein said medium is a fluid of variable density.

13. The sensor of claim 9, wherein said medium is a gas of variable density.

14. The sensor of claim 10, wherein said medium is a gas of variable density.

15. The sensor of claim 1, wherein said physical value is a level of a medium, said waveguide being submerged in said medium over part of its axial length, an optical index of refraction n of said waveguide decreasing from its lower end towards its top.

16. The sensor of claim 15, wherein said medium is a fluid.

17. The sensor of claim 15, wherein said waveguide is provided with axially adjacent sections having different optical indices of refraction n.

18. The sensor of claim 15, wherein said waveguide has a thickness d and is made of a predetermined waveguide material, said waveguide being sized in such a manner that the product of one half of said thickness d and the tangent of the total-reflection interfacial angle $\alpha TL$ of said waveguide material situated outside said medium, relative to said surrounding medium, is between one third and one fortieth of the length of said waveguide.

19. The sensor of claim 1, wherein said waveguide consists of glass.

20. The sensor of claim 1, wherein said waveguide consists of a plastic material.

21. The sensor of claim 1, wherein said waveguide comprises a transparent tube filled with a reference medium whose chemical composition corresponds, at a predetermined magnitude of said physical value, to that of a medium to be measured and surrounding said tube.

22. The sensor of claim 1, wherein said waveguide comprises light-emitting elements emitting secondary light after having been irradiated with primary light.

23. The sensor of claim 22, wherein said physical value is a length y, an optical index of refraction n of said waveguide decreasing in an axial direction, starting from a face of said wavegide, said beam of light rays impinging laterally upon said waveguide at a radial distance from said face equal to said length y, said light-sensitive elements being arranged at an axial spacing from said face.

24. The sensor of claim 23, wherein said waveguide comprises axially adjacent sections exhibiting different optical indices of refraction n.

25. The sensor of claim 23, wherein said light-emitting elements are luminescent elements.

26. The sensor of claim 24, wherein said light-emitting elements are luminescent elements 27. The sensor of claim 1, wherein said light source is connected to a pulse generator, said evaluation circuit comprising a subtractor for subtracting a first physical value measured with said light source switched off from a second physical value measured with said light source switched on.

* * * * *

UNITED STATES PATENT AND TRADEMARK OFFICE
CERTIFICATE OF CORRECTION

PATENT NO. : 4,936,681
DATED : June 26, 1990
INVENTOR(S) : Wolfgang Ruhrmann

It is certified that error appears in the above-identified patent and that said Letters Patent is hereby corrected as shown below:

In column 12, line 20, change "$\alpha$" to -- $\beta$ --.

In column 12, line 23, change "$\alpha L$" to -- $\beta L$ --.

In column 12, line 33, insert -- $\beta_0$ -- after the word "to".

Signed and Sealed this

Third Day of March, 1992

*Attest:*

HARRY F. MANBECK, JR.

*Attesting Officer*  *Commissioner of Patents and Trademarks*